United States Patent [19]

Budai et al.

[11] 4,077,999
[45] Mar. 7, 1978

[54] NOVEL OXIME ETHERS

[75] Inventors: Zoltán Budai; Aranka Lay nee Konya; Tibor Mezei; Katalin Grasser; Enikö Szirt nee Kiszelly; Ibolya Kosóczky; Lujza E. Petöcz, all of Budapest, Hungary

[73] Assignee: Egyt Gyogyszervegyeszeti Gyar, Budapest, Hungary

[21] Appl. No.: 749,399

[22] Filed: Dec. 10, 1976

Related U.S. Application Data

[62] Division of Ser. No. 652,806, Jan. 27, 1976.

[51] Int. Cl.$^2$ .................. C07C 131/02; C07C 131/04
[52] U.S. Cl. ........................... 260/566 AE; 260/501.1; 260/501.15; 424/316; 424/327
[58] Field of Search ........ 260/566 AE, 501.1, 501.15; 424/327, 316

[56] References Cited

U.S. PATENT DOCUMENTS 1,733,462  10/1929  Kropp ........................... 260/566 AE
3,429,919  2/1969   Koopman ...................... 260/566 AE
3,692,835  9/1972   Von Dijk et al. ............. 260/566 AE Primary Examiner—Gerald A. Schwartz
Attorney, Agent, or Firm—Young & Thompson

[57] ABSTRACT

The invention relates to novel oxime ethers of the formula I

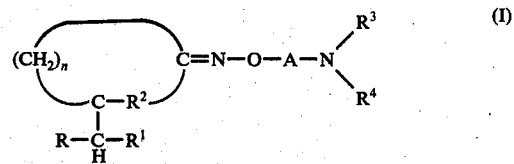

wherein
R stands for a phenyl group which may be substituted by a halogen atom or by one or more $C_1$-$C_4$ alkoxy, hydroxyl, nitro or di($C_1$-$C_3$ alkyl)amino groups,
$R^1$ and $R^2$ denote each a hydrogen atom or together a valence bond,
A denotes a $C_2$-$C_4$ straight or branched-chain alkylene group,
n denotes an integer from 3 to 10, and
$R^3$ and $R^4$ denote a hydrogen atom or a $C_1$-$C_4$ alkyl group, furthermore to acid addition salts and quaternary ammonium salts thereof. These new compounds are biologically active, and possess primarily local analgesic, spasmolytic, nicotine-lethality inhibiting, tetrabenazine-antagonistic and tetra-corspasm inhibiting effects.

2 Claims, No Drawings

NOVEL OXIME ETHERS

This application is a division of our copending application Ser. No. 652,806, filed Jan. 27, 1976.

This invention relates to novel oxime ethers possessing valuable therapeutic effects and their optical isomers, salts and quaternary ammonium derivatives.

The novel compounds have the formula I

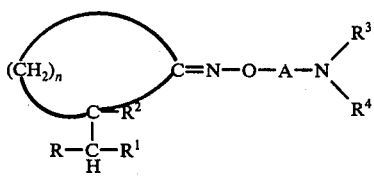

(I)

wherein
- R stands for a phenyl group which may be substituted by a halogen atom or by one or more $C_1-C_4$ alkoxy, hydroxyl, nitro or di($C_1-C_3$ alkyl)amino groups,
- $R^1$ and $R^2$ denote each a hydrogen atom or together a valence bond,
- A denotes a $C_2-C_4$ straight or branched-chain alkylene group,
- n denotes an integer from 3 to 10, and
- $R^3$ and $R^4$ denote a $C_{1-4}$ alkyl group.

The scope of the novel oxime ethers of the formula I comprises obviously also all their possible stereoisomers and mixtures thereof.

The novel compounds of the formula I can be produced in the following ways:

a. A ketone of the formula II

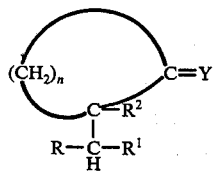

(II)

wherein R, $R^1$, $R^2$ and n have the same meaning as above, whereas Y denotes an oxygen or sulfur atom, is allowed to react with a hydroxylamine derivative of the formula III

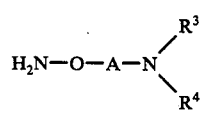

(III)

wherein A, $R^3$ and $R^4$ have the above-specified meaning.

Ketones of the formula II can be produced e.g. in the way described in J. Am. Chem. Soc. 77, 624 (1955) or in J. Chem. Soc. 1955, 1126, whereas hydroxylamine derivatives of the formula III can be prepared e.g. in the way as described in J. Pharm. Sci. 58, 138 (1969).

b. A chlorine compound of the formula IV

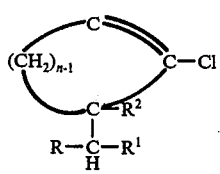

(IV)

wherein R, $R^1$, $R^2$ and n have the same meaning as above, is allowed to react with a hydroxylamine derivative of the formula III, wherein A, $R^3$ and $R^4$ have the above-specified meaning.

The compounds of formula IV can be prepared by reacting 2-(p-chlorobenzal)-cyclohexanone with phosphorous oxychloride.

c. An oxime of the formula V

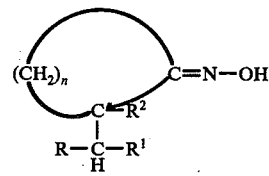

(V)

wherein R, $R^1$, $R^2$ and n have the same meaning as above, is reacted with a halogen alkylamine derivative of the formula VI

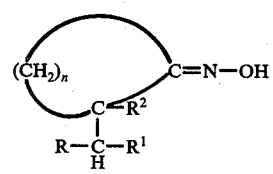

(V)

wherein R, $R^1$, $R^2$ and n have the same meaning as above, is reacted with a halogen alkylamine derivative of the formula VI $$Hal-A-N\begin{matrix}R^3\\R^4\end{matrix}$$ (VI)

wherein Hal denotes a halogen atom, preferably a chlorine atom, whereas A, $R^3$ and $R^4$ have the above-specified meanings.

The oxime of the formula V can be produced e.g. in the way described in Org. Synth. Coll. Vol. II, p. 70.

d. A compound of the formula V, wherein R, $R^1$, $R^2$ and n have the same meaning as above, is reacted with a dihaloalkane of the formula VIII $$Hal - CH_2 - A' - Hal'$$ (VIII)

wherein Hal and Hal' denote the same or different halogen atoms, whereas A' denotes a $C_1-C_3$ straight or branched-chain alkylene group, and the obtained halogen alkyl ether is aminated.

The reaction of the compounds of formulae II and III (method a/) is carried out preferably in a solvent or a solvent mixture inert for the reaction. Solvents being inert for the reaction are e.g. alcohols, preferably ethanol, or pyridine, triethyl amine etc. The temperature of the reaction can be varied within very wide limits. Though the reaction takes place according to our experience also at room temperature, the optimum reaction rate can be attained at the boiling point of the reaction mixture.

In the reaction of the compounds of the formulae IV and III (method b/) the components can be allowed to react in an inert solvent, in the presence of a base. Suitable inert solvents are e.g. diethyl ether, dibutyl ether, tetrahydrofuran, dioxane etc. or aromatic or aliphatic hydrocarbons, such as benzene, toluene, xylene, hexane, cyclohexane etc., whereas pyridine, triethyl amine, N-methylmorpholine etc. can be applied as bases. The reaction can be carried out also without any inert solvent, using only the base as a solvent. The temperature of the reaction can be varied within wide limits. The upper limit is determined by the boiling point of the reaction mixture.

When the end products are to be produced by a reaction of the compounds specified by the formulae V and VI (method c/), the reaction is to be carried out in an inert solvent, in the presence of a basic condensing agent. Benzene and its homologues, e.g. toluene, xylene, cumol etc., can be mentioned as inert solvents. In this case preferably sodium amide or sodium hydride is applied as condensing agent. Obviously the same result can be attained also by other alkali metal amides or hydrides. In that case the use of alcohols, such as ethyl, propyl, butyl alcohols, proved to be the most suitable. When an alkali hydroxide is applied as condensing agent, also water can be used as solvent.

When the compounds of the formula I are produced by reacting compounds of the formula V with those of the formula VIII (method d/), the reaction can be carried out in a solvent or a solvent mixture inert for the reaction. Benzene and its homologues, such as toluene, xylene, cumol etc. can be mentioned as inert solvents. In this case sodium amide or sodium hydride can be used as condensing agents. The same result can be attained on applying an alkali metal as condensing agent but in that case expediently ethanol is used as solvent. The amination of the obtained halogen alkyl ether is carried out under pressure in an autoclave, in the presence of the corresponding amine.

The compounds of the formula I can be converted in a known way into acid addition or quaternary ammonium salts. For the preparation of the acid addition salts physiologically tolerable acids, such as hydrogen halides, sulfuric acid, phosphoric acid, citric acid, tartaric acid, fumaric acid, maleic acid, acetic acid, propionic acid, methane sulfonic acid, succinic acid etc., can be preferably applied. In order to prepare quaternary ammonium compounds the compounds of the formula I are allowed to react with compounds suitable for quaternerization, e.g. with an alkyl halide or methane sulfonic acid ester.

The biological activity of the novel compounds according to the invention has been proved by a number of various tests. Of the observed effects the local analgesic, spasmolytic, nicotine-lethality inhibiting, tetrabenazine-antagonistic and tetracor-spasm inhibiting effects were the most significant ones.

The local analgesic effect was investigated on the ischiadic nerve of rats by means of the method of Truant and d'Amato (Truant, A.P. and Wiedling, S.: Acta Chirurg. Scand. 116, 351 /1958/). Lidocaine served as reference substance. The number of animals exhibiting typical motor paralysis and the length of the duration of this effect were recorded.

In Table I below, the relative efficiency referred to Lidocaine and the duration of the effect on application of 0.5 % and 1.0 % concentrations of Lidocaine are given. Also the toxicity values observed on oral administration are shown.

Table I

| Compound (in Example) | $LD_{50}$ mg/kg | Relative efficiency | Duration, minutes (0.5%) | Duration, minutes (1.0%) |
|---|---|---|---|---|
| 7 | 210 | 1.8 | 94 | 127 |
| 2 | 430 | 3.2 | 72 | 111 |
| 5 | 450 | 1.8 | 68 | 96 |
| 6 | 950 | 2.1 | 88 | 113 |
| 1 | 560 | 1.7 | 99 | 115 |

Table I-continued

| Compound (in Example) | $LD_{50}$ mg/kg | Relative efficiency | Duration, minutes (0.5%) | Duration, minutes (1.0%) |
|---|---|---|---|---|
| 8 | 450 | 1.1 | 66 | 129 |
| 15 | 880 | 1.7 | 92 | 160 |
| Lidocaine | 220 | 1.0 | 28 | 52 |

$$\text{Relative efficiency} = \frac{EC_{50} \text{ Lidocaine}}{EC_{50} \text{ examined compound}}$$

The spasmolytic effect on non-striated muscles was determined in isolated rat-ileum by the method of Brock et al. (Brock, N., Geks, J. and Lorenz, D.: Arch. Exper. Path. u. Pharmacol. 215, 492 /1952/), applying papaverine as reference substance. In order to characterize the efficiency of an individual compound, the efficiency related to that of papaverine and the $LD_{50}$ values observed on oral administration are shown in Table II.

Table II

| Compound (in Example) | $LD_{50}$ p.o. | Relative efficiency |
|---|---|---|
| 11 | 325 | 3.01 |
| 18 | 650 | 2.43 |
| 10 | 550 | 2.42 |
| 13 | 1000 | 1.96 |
| 2 | 430 | 1.73 |
| Papaverine | 367 | 1.00 |

$$\text{Relative efficiency} = \frac{EC_{50} \text{ papaverine}}{EC_{50} \text{ examined compound}}$$

The inhibition of nicotine lethality was determined on mice by the method of Stone (Stone, C.A. et al.: Arch. Intern. Pharmacodyn. 117, 419 /1958/) in groups of ten mices each, at oral administration. The results are given in Table III.

Table III

| Compound (in Example) | $LD_{50}$ mg/kg | $ED_{50}$ mg/kg | Therapeutic index |
|---|---|---|---|
| 12 | 1450 | 40 | 36.3 |
| 27 | 600 | 47 | 12.8 |
| 4 | 400 | 11 | 36.4 |
| Trihexyphenidyl (Artane) | 365 | 40 | 9.13 |

Therapeutic index = $LD_{50}/ED_{50}$

The tetrabenazine-reserpine antagonistic effect was investigated on mice in groups of ten animals each, at oral administration. The inhibition or suspension of the effect of the observed maximum dose was recorded, and the $ED_{50}$ values were calculated on the basis of the dose vs. effect curves. The results are shown in Table IV.

Table IV

| Compound (in Example) | $LD_{50}$ mg/kg | Tetrabenazine antagonism, $ED_{50}$ mg/kg | Therapeutic index | Reserpine antagonism $ED_{50}$, mg/kg | Therapeutic index |
|---|---|---|---|---|---|
| 13 | 1000 | 70 | 14.3 | 80 | 12.5 |
| 1 | 560 | 80 | 7.0 | 27 | 20.7 |
| 27 | 600 | 120 | 5.0 | 18 | 33.0 |
| 19 | 900 | 34 | 26.5 | over 180 | 5.0 |
| 21 | 1500 | 22 | 68.2 | over 100 | 15.0 |
| Amitriptylin | 225 | 13 | 17.3 | 65 | 3.5 |

The new compounds of formula I and their methods of preparation are further illustrated by the aid of the following non-limiting Examples.

EXAMPLE 1

2-Benzal-1-(3'-dimethylaminopropoxyimino)-cyclohexane

The solution of 20.1 g (0.1 moles) of 2-benzalcyclohexanone-oxime in 200 ml of anhydrous toluene is dropwise added at 85° C, under continuous stirring, to a suspension of 2.4 g (0.1 moles) of sodium hydride in 50 ml of anhydrous toluene. The mixture is kept for 2 hours at 130° C, and on further continuing the stirring, a solution of 13.3 g (0.11 moles) of dimethylaminopropyl chloride in 40 % anhydrous toluene is added. On heating the mixture for further 6 hours, the toluene solution is cooled to 30° C, washed with 100 ml of water, and extracted with an aqueous solution of 15 g (0.1 moles) of tartaric acid or with an equivalent amount of diluted aqueous hydrochloric acid. The aqueous solution cooled to 0°-5° C is made alkaline to pH 10 with ammonium hydroxide, and the separating oily base extracted with dichloroethane. On distilling off the solvent, the residue is fractionated under vacuum. Yield: 19.6 g (68.6%); b.p.: 182°-186° C at 0.4 torr.

Fumarate: m.p. 134°-135° C. Analysis: $C_{22}H_{30}N_2O_5$ Calculated: C 65.81%, H 7.53 %, N 6.98 %, Found: C 65.61 %, H 7.65 %, N 7.03 %.

EXAMPLE 2

2-Benzal-1-(2'-diethylaminoethoxyimino)-cyclohexane

One proceeds according to Example 1, with the difference that, instead of dimethylaminopropyl chloride, 14.9 g (0.11 moles) of diethylaminoethyl chloride are applied.

Yield: 16.8 g (62.4 %) of a yellow oil. B.p.: 192°-196° C at 0.4 torr. Fumarate: m.p. 110°-112° C. Analysis: $C_{23}H_{32}N_2O_5$ Calculated: C 66.33 %, H 7.74 %, N 6.72 %, Found: C 66.16 %, H 7.87 %, N 6.75 %.

EXAMPLE 3

2-Benzal-1-(2'-dimethylaminoethoxyimino)-cyclohexane

One proceeds according to Example 1, with the difference that, instead of dimethylaminopropyl chloride, 11.8 g (0.11 moles) of dimethylaminoethyl chloride are applied.

Yield: 20 g (73.9 %) of a yellow oil. B.p.: 174°-176° C at 0.3 torr. Fumarate: m.p. 140°-142° C. Analysis: $C_{21}H_{28}N_2O_5$ Calculated: C 64.92 %, H 7.27 %, N 7.21 %, Found: C 64.92 %, H 7.16 %, N 7.27 %.

EXAMPLE 4

1-(2'-Aminoethoxyimino)-2-benzalcyclohexane

To a sodium methylate solution prepared from 9.2 g (0.4 moles) of sodium metal and 200 ml of anhydrous ethanol, 20.1 g (0.1 moles) of 2-benzalcyclohexanone oxime and 23.2 g (0.2 moles) of β-chloroethylamine hydrochloride are added at room temperature. The mixture is stirred for four hours at room temperature, then the sodium chloride is removed by filtration and the solution is evaporated under vacuum. The residue is mixed up with water, extracted with chloroform, and evaporated.

Yield: 25 g (50 %). Hemifumarate: m.p. 165° C. Analysis: $C_{17}H_{22}O_3N_2$ Calculated: C 67.50 %, H 7.30 %, N 9.27 %, Found: C 67.45 %, H 7.18 %, N 9.35 %.

EXAMPLE 5

2-Benzal-1-(2'-dimethylaminoethoxyimino)-cyclopentane

A sodium salt is prepared in the usual way from 2.4 g (0.1 moles) of sodium hydride and 18.7 g (0.1 moles) of 2-benzalcyclopentanone oxime in a toluene medium, and then allowed to react with 11.8 g (0.11 moles) of dimethylaminoethyl chloride. Subsequently one proceeds in the way specified in Example 1.

Yield: 16.1 g (62.2 %) of a yellow oil. B.p.: 172°-174° C at 0.3 torr. Fumarate: m.p. 125°-127° C. Analysis: $C_{20}H_{26}N_2O_5$ Calculated: C 64.18 %, H 7.00 %, N 7.48 %, Found: C 64.33 %, H 7.13 %, N 7.43 %.

EXAMPLE 6

2-Benzal-1-(2'-dimethylaminopropoxyimino)-cyclopentane

A sodium salt is prepared from 2.4 g (0.1 moles) of sodium hydride and 18.7 g (0.1 moles) of 2-benzalcyclopentanone oxime in a toluene medium, then allowed to react with 18.2 g (0.17 moles) of dimethylaminopropyl chloride, Subsequently one proceeds in the way specified in Example 1.

Yield: 23.65 g (57.9 %) of a yellow viscous oil. B.p.: 193°-194° C at 0.4 torr. Fumarate: m.p. 122°-124° C. Analysis: $C_{21}H_{28}N_2O_5$ Calculated: C 64.95 %, H 7.26 %, N 7.21 %, Found: C 64.93 %, H 7.20 %, N 7.08 %.

EXAMPLE 7

2-Benzal-1-(2'-diethylaminoethoxyimino)-cyclopentane

On starting from 2.4 g (0.1 moles) of sodium hydride, 18.7 g (0.1 moles) of 2-benzalcyclopentanone oxime and 14.9 g (0.11 moles) of diethylaminoethyl chloride, one proceeds in the way as specified in Example 1.

Yield: 26.8 g (75 %). B.p.: 178°-180° C at 0.3 torr. Fumarate: m.p. 123°-124° C. Analysis: $C_{22}H_{30}N_2O_5$ Calculated: C 65.65 %, H 7.51%, N 6.96 %, Found: C 65.83 %, H 7.67 %, N 6.95 %.

EXAMPLE 8

2-Benzal-1-(2'-diisopropylaminoethoxyimino)-cyclopentane

On starting from 2.4 g (0.1 moles) of sodium hydride, 18.7 g (0.1 moles) of 2-benzalcyclopentanone oxime and 18.01 g (0.11 moles) of diisopropylaminoethyl chloride, one proceeds in the way as specified in Example 1.

Yield: 18.7 g (59.4 %). B.p.: 197°-198° C at 0.3 torr. Fumarate: m.p. 123°-125° C. Analysis: $C_{24}H_{34}N_2O_5$ Calculated: C 66.97 %, H 7.96 %, N 6.51 %. Found: C 66.73 %, H 7.95 %, N 6.46 %.

EXAMPLE 9

2-Benzal-1-(2'-dimethylaminoethoxyimino)-cycloheptane

One proceeds in the way as specified in Example 1, with the difference that 21.5 g (0.1 moles) of 2-benzalcycloheptanone oxime and 11.8 g (0.11 moles) of dimethylaminoethyl chloride are applied.

Yield: 20 g (69.6 %). Fumarate: m.p. 130°-132° C. Analysis: $C_{22}H_{30}N_2O_5$ Calculated: C 65.60 %, H 7.52 %, N 6.98 %. Found: C 65.60 %, H 7.73 %, N 6.87 %.

EXAMPLE 10

2-Benzal-1-(3'-dimethylaminopropoxyimino)-cycloheptane

One proceeds in the way as specified in Example 1, with the difference that, instead of 2-benzalcyclohexanone oxime, 21.5 g (0.1 moles) of 2-benzalcycloheptanone oxime is applied.

Yield: 16.7 g (72.4 %) of a yellow oil. B.p.: 178°–180° C at 0.2 torr. Fumarate: m.p. 134°–135° C. Analysis: $C_{23}H_{32}N_2O_5$ Calculated: C 66.34%, H 7.74 %, N 6.72 %. Found: C 66.23 %, H 7.80 %, N 6.66 %.

EXAMPLE 11

2-Benzal-1-(2'-diisopropylaminoethoxyimino)-cycloheptane

On starting from 2.4 g (0.1 moles) of sodium hydride, 21.5 g (0.1 moles) of 2-benzalcycloheptanone oxime and 17.95 g (0.11 moles) of diisopropylaminoethyl chloride, one proceeds in the way as specified in Example 1.

Yield: 26.0 g (76.2 %) of a yellow oil. Fumarate: m.p. 132°–134° C. Analysis: $C_{26}H_{38}N_2O_5$ Calculated: C 68.08 %, H 8.35 %, N 6.11 %. Found: C 68.16 %, H 8.46 %, H 6.07 %.

EXAMPLE 12

1-(3'-Dimethylaminopropoxyimino)-2-(p-chlorobenzal)-cycloheptane

One proceeds in the way as specified in Example 1, with the difference that, instead of 2-benzalcyclohexanone oxime, 24.9 g (0.1 moles) of 2-(p-chlorobenzal)-cycloheptanone oxime are applied.

Yield: 16.06 g (60.1 %) of a yellow oil. Fumarate: m.p. 159°–160° C. Analysis: $C_{23}H_{31}ClN_2O_5$ Calculated: C 61.22 %, H 6.94 %, N 6.22 %, Cl 7.86 %. Found: C 61.44 %, H 7.09 %, N 6.12 %, Cl 7.86%.

EXAMPLE 13

1-(3'-Dimethylaminopropoxyimino)-2-(p-methoxybenzal)-cycloheptane

One proceeds in the way as specified in Example 1, with the difference that, instead of 2-benzalcyclohexanone oxime, 24.5 g (0.1 moles) of 2-(p-methoxybenzal)-cycloheptanone oxime are applied.

Yield: 15.6 g (67.5 %) of a yellow oil. Fumarate: m.p. 133°–135° C. Analysis: $C_{24}H_{34}N_2O_6$ Calculated: C 64.57 %, H 7.67 %, N 6.27 %. Found: C 64.39 %, H 7.84 %, N 6.18 %.

EXAMPLE 14

1-(2'-Diethylaminoethoxyimino)-2-(o-methoxybenzal)-cyclohexane

On starting from 2.4 g (0.1 moles) of sodium hydride, 23.1 g (0.1 moles) of 2-(o-methoxybenzal)-cyclohexanone oxime and 14.9 g (0.11 moles) of diethylaminoethyl chloride, one proceeds in the way as specified in Example 1.

Yield: 21 g (65.1 %). Fumarate: m.p.: 142°–143° C. Cyclamate: m.p. 126°–127° C. Analysis: $C_{24}H_{34}N_2O_6$ Calculated: C 64.50 %, H 7.64 %, N 6.28 %. Found: C 64.02 %, H 8.08 %, N 6.23 %.

EXAMPLE 15

1-(3'-Dimethylaminopropoxyimino)-2-(o-methoxybenzal)-cyclohexane

On starting from 2.4 g (0.1 moles) of sodium hydride, 23.1 g (0.1 moles) of 2-(p-methoxybenzal)-cyclohexanone oxime and 13.3 g (0.11 moles) of dimethylaminopropyl chloride, one proceeds in the way as specified in Example 1.

Yield: 22.6 g (71.6 %). B.p.: 185°–190° C at 0.05 torr. Fumarate: m.p. 122°–123° C. Analysis: $C_{23}H_{32}N_2O_6$ Calculated: C 63.86 %, H 7.45 %, N 6.48 %. Found: C 63.78 %, H 7.67 %, N 6.42 %.

EXAMPLE 16

1-(3'-Dimethylaminopropoxyimino)-2-(m-methoxybenzal)-cyclohexane

On starting from 2.4 g (0.1 moles) of sodium hydride, 23.1 g (0.1 moles) of 2-(m-methoxybenzal)-cyclohexanone oxime and 13.3 g (0.11 moles) of dimethylaminopropyl chloride, one proceeds in the way as specified in Example 1.

Yield: 28.2 g (39.3 %). Fumarate: m.p. 115°–116° C. Analysis: $C_{23}H_{32}N_2O_6$ Calculated: C 63.86 %, H 7.45 %, H 6.48 %. Found: C 63.42 %, H 7.27 %, N 6.45 %.

EXAMPLE 17

1-(2'-Methyl-3'-dimethylaminopropoxyimino)-2-(p-methoxybenzal)-cyclohexane

On starting from 2.4 g (0.1 moles) of sodium hydride, 23.1 g (0.1 moles) of 2-(p-methoxybenzal)-cyclohexanone oxime and 16.5 g (0.11 moles) of dimethylaminoisobutyl chloride, one proceeds in the way as specified in Example 1.

Yield: 22.4 g (68 %). B.p.: 189° C at 0.05 torr. Fumarate: m.p. 153°–154° C. Analysis: $C_{24}H_{34}N_2O_6$ Calculated: C 64.74%, H 7.66 %, N 6.26 %. Found: C 64.34 %, H 7.73 %, N 6.30 %.

EXAMPLE 18

1-(2'-Methyl-3'-dimethylaminopropoxyimino)-2-(o-methoxybenzal)-cyclohexane

On starting from 2.4 g (0.1 moles) of sodium hydride, 23.1 g (0.1 moles) of 2-(o-methoxybenzal)-cyclohexanone oxime and 16.5 g (0.11 moles) of dimethylaminoisobutyl chloride, one proceeds in the way as specified in Example 1.

Yield: 30.0 g (90 %) Fumarate: m.p. 159°–160° C. Maleinate: m.p. 113°–114° C. Analysis: $C_{24}H_{34}N_2O_6$ Calculated: C 64.74 %, H 7.66 %, N 6.26 %. Found: C 64.25 %, H 7.54 %, N 6.38 %.

EXAMPLE 19

1-(Dimethylaminopropoxyimino)-2-(p-chlorobenzal)-cyclohexane

A solution of 23.5 g (0.1 moles) of 2-(p-chlorobenzal)-cyclohexanone oxime in 200 ml of anhydrous toluene is added dropwise at 85° C under stirring, to a suspension of 2.4 g (0.1 moles) of sodium hydride in 50 ml of anhydrous toluene. The mixture is kept for two hours at 130° C, then a solution of 13.3 g (0.11 moles) of dimethylaminopropyl chloride in 50 ml of anhydrous toluene is added. The mixture is kept for 12 hours at 130° C, then cooled and shaken with a solution of 35 g of tartaric acid in 150 ml of water. The aqueous phase is cooled to 0°–5° C and made alkaline to pH 10 with ammonium hydroxide. After extraction with dichloroethane, the solvent is distilled off.

Yield: 24.3 g (76.0 %). Fumarate: m.p. 142°–143° C. Analysis: $C_{22}H_{29}ClN_2O_5$ Calculated: C 60.47 %, H 6.69 %, Cl 8.11 %, N 6.41 %. Found: C 60.67 %, H 6.87 %, Cl 8.2 %, N 6.43 %.

EXAMPLE 20

1-(Dimethylaminopropoxyimino)-2-(m-chlorobenzal)-cyclohexane

On starting from 2.4 g (0.1 moles) of sodium hydride, 23.5 g (0.1 moles) of 2-(m-chlorobenzal)-cyclohexanone oxime and 13.3 g (0.11 moles) of dimethylaminopropyl chloride, one proceeds in the way as specified in Example 1.

Yield: 23.0 g (72 %). Fumarate: m.p. 142°–144° C. Analysis: $C_{22}H_{29}ClN_2O_5$ Calculated: C 60.47 %, H 6.69 %, Cl 8.11 %, N 6.41 %. Found: C 60.58 %, H 6.90 %, Cl 8.20 %, N 6.22 %.

EXAMPLE 21

1-(Dimethylaminopropoxyimino)-2-(o-chlorobenzal)-cyclohexane

On starting from 2.4 g (0.1 moles) of sodium hydride, 23.5 g (0.1 moles) of 2-(o-chlorobenzal)-cyclohexanone oxime and 13.3 g (0.11 moles) of dimethylaminopropyl chloride, one proceeds in the way as specified in Example 1.

Yield: 21.5 g (67.2 %). Fumarate: m.p. 112°–113° C. Analysis: $C_{22}H_{29}ClN_2O_5$ Calculated: C 60.47 %, H 6.69 %, Cl 8.11 %, N 6.41 %. Found C 60.25 %, H 6.47 %, Cl 8.10 %, N 6.35 %.

EXAMPLE 22

2-Benzyl-1-(2'-dimethylaminoethoxyimino)-cyclohexane

One proceeds in the way specified in Example 1, starting from the following substances: 2.4 g (0.1 moles) of sodium hydride, 20.2 g (0.1 moles) of 2-benzylcyclohexanone oxime and 11.83 g (0.11 moles) of dimethylaminoethyl chloride.

Yield: 20.4 g (74.5 %). B.p.: 174°–176° C at 0.3 torr. Fumarate: m.p. 133°–134° C Analysis: $C_{21}H_{30}N_2O_5$ Calculated: C 64.52 %, H 7.75 %, N 7.18 %. Found: C 64.71 %, H 7.80 %, N 7.15 %.

EXAMPLE 23

2-Benzyl-1-(3'-dimethylaminopropoxyimino)-cyclohexane

One proceeds in the way as specified in Example 1, starting from the following substances: 2.4 g (0.1 moles) of sodium hydride, 20.2 g (0.1 moles) of 2-benzylcyclohexanone oxime, and 13.36 g (0.11 moles) of dimethylaminopropyl chloride.

Yield: 23.7 g (82.3 %). B.p.: 172°–174° C at 0.4 torr. Fumarate: m.p. 134°–136° C. Analysis: $C_{22}H_{32}N_2O_5$ Calculated: C 65.4 %, H 8.32 %, N 6.97 %. Found: C 65.5 %, H 8.10 %, N 6.95 %.

EXAMPLE 24

DL-2-Benzyl-1-(2'-methyl-3'-dimethylaminopropoxyimino)-cyclohexane

One proceeds in the way as specified in Example 1, starting from the following substances: 2.4 g (0.1 moles) of sodium hydride, 20.2 g (0.1 moles) of 2-benzylcyclohexanone oxime, and 14.91 g (0.11 moles) of 2-methyl-3-dimethylaminopropyl chloride.

Yield: 24.1 g (80.0 %). B.p.: 150°–155° C at 0.05 torr. Fumarate: m.p. 166°–167° C. Analysis: $C_{23}H_{34}N_2O_5$ Calculated: C 66.1 %, H 8.15 %, N 6.7 %. Found: C 66.3 %, H 8.29 %, N 6.6 %.

EXAMPLE 25

DL-2-(p-Methoxybenzyl)-1-(2'-methyl-3'-dimethylaminopropoxy)-cyclohexane

One proceeds in the way as specified in Example 1, starting from the following substances: 2.4 g (0.1 moles) of sodium hydride, 23.63 g (0.1 moles) of 2-(p-methoxybenzyl)-cyclohexanone oxime, and 14.91 g (0.11 moles) of 2-methyl-3-dimethylaminopropyl chloride.

Yield: 26.9 g (81.0 %). B.p.: 168°–170° C at 0.05 torr. Analysis: $C_{24}H_{36}N_2O_6$ Calculated: C 64.3 %, H 8.10 %, N 6.25 %. Found: C 64.4 %, H 8.25 %, N 6.18 %.

EXAMPLE 26

2-(p-Methoxybenzyl)-1-(3'-dimethylaminopropoxyimino)-cyclohexane

One proceeds in the way as specified in Example 1, starting from the following substances: 2.4 g (0.1 moles) of sodium hydride, 23.63 g (0.1 moles) of 2-(p-methoxybenzyl)-cyclohexanone oxime, and 13.36 g (0.11 moles) of dimethylaminopropyl chloride.

Yield: 22.65 g (72 %). B.p.: 184°–185° C at 0.4 torr. Fumarate: m.p. 89°–91° C. Analysis: $C_{23}H_{34}N_2O_6$ Calculated: C 63.75 %, H 7.80 %, N 6.45 %. Found: C 63.50 %, H 7.76 %, N 6.45 %.

EXAMPLE 27

2-Benzal-1-(2'-dimethylaminoethoxyimino)-cyclopentane 34.4 g (0.2 moles) of 2-benzalcyclopentanone and 35.4 g (0.2 moles) of dimethylaminoethoxyamine hydrochloride are boiled for three hours in a mixture of 300 ml of anhydrous ethanol and 150 ml of pyridine, then the mixture is evaporated under vacuum. The residue is made alkaline, the base extracted with chloroform, then the solvent removed by distillation.

Yield: 50 g (95.2 %). Fumarate: m.p. 126°–127° C. Analysis: $C_{20}H_{26}N_2O_5$ Calculated: C 64.18 %, H 7.00 %, N 7.48 %. Found: C 64.03 %, H 7.25 %, N 7.39 %.

EXAMPLE 28

2-Benzal-1-(2'-methyl-3'-dimethylaminopropoxyimino)-cyclohexane

One proceeds in the way specified in Example 1, with the difference that, instead of dimethylaminopropyl chloride, 16.5 g (0.11 moles) of dimethylaminoisobutyl chloride are applied.

Yield: 21 g (70 %) of a yellow oil. B.p.: 182° C at 0.4–0.5 torr. Fumarate: m.p. 77°–78° C. Citrate: m.p. 98°–99° C. Iodomethylate: m.p. 163°–164° C. Analysis: $C_{23}H_{32}N_2O_5$ Calculated: C 66.33 %, H 7.74 %, N 6.72 %. Found: C 66.18 %, H 7.82 %, N 6.66 %.

EXAMPLE 29

2-(p-Methoxybenzal)-1-(3'-dimethylaminopropoxyimino)-cyclohexane

On starting from 2.4 g (0.1 moles) of sodium hydride, 23.1 g (0.1 moles) of 2-(p-methoxybenzal)-cyclohexanone oxime and 13.3 g (0.11 moles) of dimethylaminopropyl chloride, one proceeds in the way as specified in Example 1.

Yield: 24.5 g (77.5 %). Fumarate: m.p. 125°–126° C. Analysis: $C_{23}H_{32}N_2O_6$ Calculated: C 63.94 %, H 7.92 %, N 6.47 %. Found: C 64.00 %, H 7.83 %, N 6.41 %.

EXAMPLE 30

2-(o-Chlorobenzal)-1-(3'-dimethylaminoethoxyimino)-cyclohexane

On starting from 2.4 g (0.1 moles) of sodium hydride, 23.5 g (0.1 moles) of 2-(o-chlorobenzal)-cyclohexanone oxime and 11.8 g (0.11 moles) of dimethylaminoethyl chloride, one proceeds in the way as specified in Example 1.

Yield: 23.38 g (76.25 %). Fumarate: m.p. 126°–128° C. Analysis: $C_{21}H_{24}ClN_2O_5$ Calculated: C 59.64 %, H 5.72%, Cl 8.39 %, H 6.62 %. Found: C 59.52 %, H 5.90%, Cl 8.40 %, H 6.58 %.

EXAMPLE 31

2-(p-Chlorobenzyl)-1-(3'-dimethylaminopropoxyimino)-cyclohexane

On starting from 2.4 g (0.1 moles) of sodium hydride, 23.7 g (0.1 moles) of 2-(p-chlorobenzyl)-cyclohexanone oxime and 13.3 g (0.11 moles) of dimethylaminopropyl chloride, one proceeds in the way as specified in Example 1.

Yield: 25.4 g (79 %) of a yellow oil B.p.: 160° C at 0.2 torr. Fumarate: m.p. 143°–144° C. Analysis: $C_{22}H_{31}ClN_2O$ Calculated: C 62.25 %, H 7.37 %, Cl 8.35 %, N 3.30 %. Found: C 62.37 %, H 7.40 %, Cl 8.27 %, N 3.28 %.

EXAMPLE 32

2-Benzal-1-(2'-dimethylaminoethoxyimino)-cyclohexane 20.23 g (0.1 moles) of 2-benzalcyclohexathione and 17.7 g (0.1 moles) of dimethylaminoethoxyamine hydrochloride are boiled for several hours in a mixture of 150 ml of anhydrous ethanol and 75 ml of anhydrous pyridine, then the solvents removed under vacuum. The evaporation residue is made alkaline to pH 10 with an aqueous solution of an alkali hydroxide, the base extracted with dichloroethane, then the extract liberated from the solvent.

Yield: 22.3 g (81.5 %) of a pale yellow oil. B.p.: 174°–176° C at 0.3 torr.

The 2-benzalcyclohexathione serving as a starting substance is prepared as follows:

60 g (0.565 moles) of freshly distilled benzaldehyde, and 101.5 g (0.89 moles) of cyclohexathione are allowed to react for 3 hours at the boiling point of the mixture, in the presence of 20 g of potassium hydroxide in 350 ml of water, then the reaction mixture is cooled to room temperature and neutralized with 70 ml of 18 % hydrochloric acid. The mixture is subsequently extracted with 3×50 ml of dichloroethane, the extracts are combined and the solvent is removed under vacuum. The residue is purified by vacuum fractionation.

Yield: 112.5 g (62.5 %) of a yellow, slow crystallizing oil. B.p.: 152°–157° C at 0.4 torr.

EXAMPLE 33

2-(p-Chlorobenzal)-1-(3'-dimethylaminopropoxyimino)-cyclohexane 17.6 g (0.08 moles) of 2-(p-chlorobenzal)-cyclohexanone are kept for an hour at 100° C with 65 ml of phosphorous oxychloride, then excess phosphorous oxychloride is removed by vacuum distillation at 50° C. The residue is treated at a temperature between 0° and 10° C with 65 ml of anhydrous pyridine and 19.8 g (0.11 moles) of 3'-dimethylaminopropoxyamine dihydrochloride, then the mixture kept for an hour at 50° C and boiled for another hour. The residue is dissolved in some water and made alkaline with 2 N sodium hydroxide solution. After extraction with 3×35 ml of dichloroethane, the combined dichloroethane solutions are distilled under vacuum until the solvent is removed.

Yield: 27.2 g (85 %) of a yellow viscous oil. Fumarate: m.p. 142°–143° C.

EXAMPLE 34

1-(N-Dimethylaminoethoxyimino)-2-(p-nitrobenzal)-cyclohexane

On starting from 17.7 g (0.1 moles) of dimethylaminoethoxyamine hydrochloride and 23.1 g (0.1 moles) of 2-(p-nitrobenzal)-cyclohexanone, one proceeds in the way as specified in Example 32.

Yield: 21 g (70 %) Fumarate: m.p. 148°–150° C. Analysis: $C_{21}H_{27}N_3O_6$ Calculated: C 60.42 %, H 6.52 %, N 10.07 %. Found: C 60.57 %, H 6.48 %, N 9.92 %.

What we claim is:

1. A novel oxime ether of the formula I

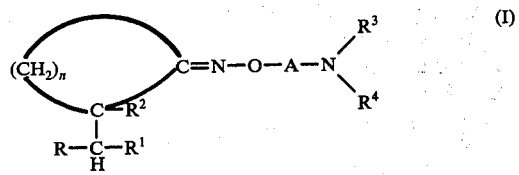

wherein
R stands for a phenyl group which may be substituted by a halogen atom or by one or more $C_1$–$C_4$ alkoxy, hydroxyl, nitro or di($C_1$–$C_3$ alkyl)amino groups,
$R^1$ and $R^2$ denote each a hydrogen atom or together a valence bond,
A denotes a $C_2$–$C_4$ straight or branched-chain alkylene group,
n denotes an integer from 3 to 10, and
$R^3$ and $R^4$ denote a $C_1$–$C_4$ alkyl group, or a pharmaceutically acceptable acid addition salt or quaternary ammonium salt thereof.

2. 2-Benzal-1-(2'-diethylaminoethoxyimino)-cyclohexane or a pharmaceutically acceptable acid addition salt thereof.

* * * * *